(12) United States Patent
Dixon et al.

(10) Patent No.: US 11,058,292 B2
(45) Date of Patent: Jul. 13, 2021

(54) VIDEO LARYNGOSCOPES

(71) Applicant: INTERSURGICAL AG, Vaduz (LI)

(72) Inventors: Phillip William Dixon, Wokingham (GB); Mark Richard Browne, Wokingham (GB); Andrew Neil Miller, Wokingham (GB)

(73) Assignee: INTERSURGICAL AG, Vaduz (LI)

( * ) Notice: Subject to any disclaimer, the term of this patent is extended or adjusted under 35 U.S.C. 154(b) by 109 days.

(21) Appl. No.: 15/575,606

(22) PCT Filed: May 17, 2016

(86) PCT No.: PCT/EP2016/061015
§ 371 (c)(1),
(2) Date: Nov. 20, 2017

(87) PCT Pub. No.: WO2016/184851
PCT Pub. Date: Nov. 24, 2016

(65) Prior Publication Data
US 2018/0153389 A1 Jun. 7, 2018

(30) Foreign Application Priority Data

May 21, 2015 (GB) .................................. 1508739

(51) Int. Cl.
*A61B 1/267* (2006.01)
*A61B 1/04* (2006.01)
*A61B 1/00* (2006.01)

(52) U.S. Cl.
CPC .......... *A61B 1/267* (2013.01); *A61B 1/00045* (2013.01); *A61B 1/00103* (2013.01); *A61B 1/04* (2013.01); *A61B 1/042* (2013.01)

(58) Field of Classification Search
CPC ....... A61B 1/267; A61B 1/00103; A61B 1/04; A61B 1/00045
(Continued)

(56) References Cited

U.S. PATENT DOCUMENTS

| 5,827,178 A | 10/1998 | Berall |
| 6,840,903 B2 | 1/2005 | Mazzei et al. |

(Continued)

FOREIGN PATENT DOCUMENTS

| CN | 101175159 A | 5/2008 |
| CN | 101472062 A | 7/2009 |

(Continued)

OTHER PUBLICATIONS

Great Britain Search Report corresponding to GB1508739.8, dated Nov. 13, 2015.

(Continued)

*Primary Examiner* — Matthew J Lawson
(74) *Attorney, Agent, or Firm* — Troutman Pepper Hamilton Sanders LLP (Rochester)

(57) ABSTRACT

A laryngoscope (10) having a body (20, 42) including a handle, a laryngoscope blade (22) extending from a distal end of the body (20, 42), and a display screen housing (18) extending from a proximal end of the body (20, 42). The laryngoscope (10) has at least one unitary housing component (12) that defines at least a portion of each of the body (20, 42), the laryngoscope blade (22) and the display screen housing (18).

18 Claims, 8 Drawing Sheets

(58) Field of Classification Search
USPC .................................................. 606/184, 188
See application file for complete search history.

(56) References Cited

U.S. PATENT DOCUMENTS

| | | | |
|---|---|---|---|
| 7,946,981 B1 | 5/2011 | Cubb | |
| 2005/0043590 A1 | 2/2005 | Mazzei et al. | |
| 2009/0032016 A1* | 2/2009 | Law | A61M 16/0488 128/200.26 |
| 2010/0261967 A1 | 10/2010 | Pacey et al. | |
| 2011/0152620 A1* | 6/2011 | Dhonneur | A61B 1/00052 600/194 |
| 2012/0130160 A1* | 5/2012 | Borrye | A61B 1/00062 600/103 |
| 2012/0316398 A1 | 12/2012 | Ashcraft et al. | |
| 2013/0057667 A1 | 3/2013 | McGrath | |
| 2013/0197312 A1 | 8/2013 | Miller et al. | |
| 2013/0345518 A1 | 12/2013 | Law et al. | |
| 2014/0194694 A1* | 7/2014 | Chen | A61B 1/053 600/188 |
| 2015/0080655 A1 | 3/2015 | Peterson et al. | |
| 2016/0051781 A1* | 2/2016 | Isaacs | A61M 16/0488 600/188 |
| 2016/0317010 A1 | 11/2016 | McGrath | |

FOREIGN PATENT DOCUMENTS

| | | |
|---|---|---|
| CN | 201780482 U | 3/2011 |
| CN | 102068231 A | 5/2011 |
| CN | 102547020 A | 7/2012 |
| CN | 102984994 | 3/2013 |
| CN | 204275225 | 4/2015 |
| EP | 2380486 A | 10/2011 |
| GB | 2354448 A | 3/2001 |
| GB | 2431539 A | 4/2007 |
| GB | 2431540 A | 4/2007 |
| GB | 2431541 A | 4/2007 |
| WO | 2009/027669 A2 | 3/2009 |
| WO | 2010/093554 A2 | 8/2010 |
| WO | 2010/114867 A1 | 10/2010 |
| WO | 2011/066510 A2 | 6/2011 |
| WO | 2011/141686 A1 | 11/2011 |
| WO | 2011/141751 A2 | 11/2011 |
| WO | 2011/141753 A1 | 11/2011 |
| WO | 2011141686 A1 | 11/2011 |
| WO | 2013/072706 A1 | 5/2013 |
| WO | 2014/191773 A1 | 12/2014 |

OTHER PUBLICATIONS

PCT International Search Report and Written Opinion corresponding to PCT/EP2016/061015, dated Jul. 14, 2016.
International Preliminary Report on Patentability for PCT/EP2016/061015 (dated Nov. 21, 2017).
Office Action for GB Application No. GB1508739.8, dated Jul. 12, 2019.
Chinese Office Action for Corresponding CA Application No. 2016800426181, dated Nov. 17, 2020, 13 pages.
European Search Report for Corresponding European Application No. 16722011.1, dated Dec. 31, 2020, 2 pages.

* cited by examiner

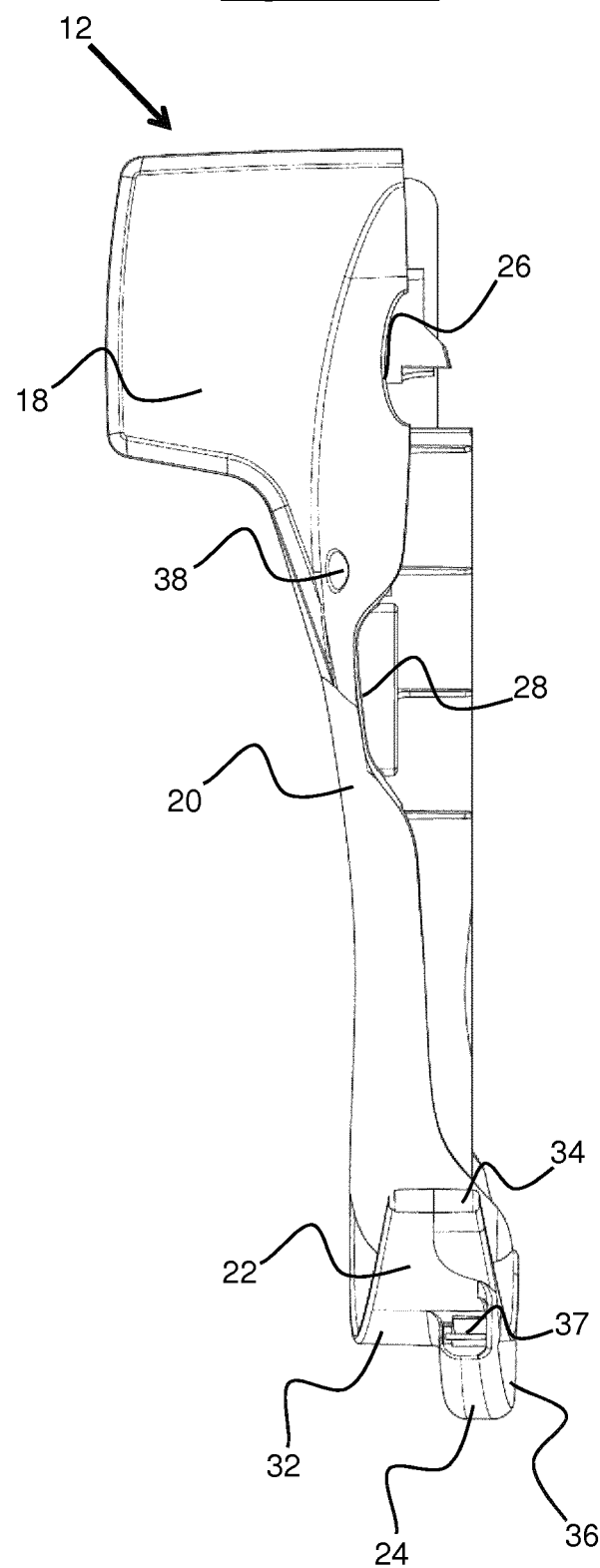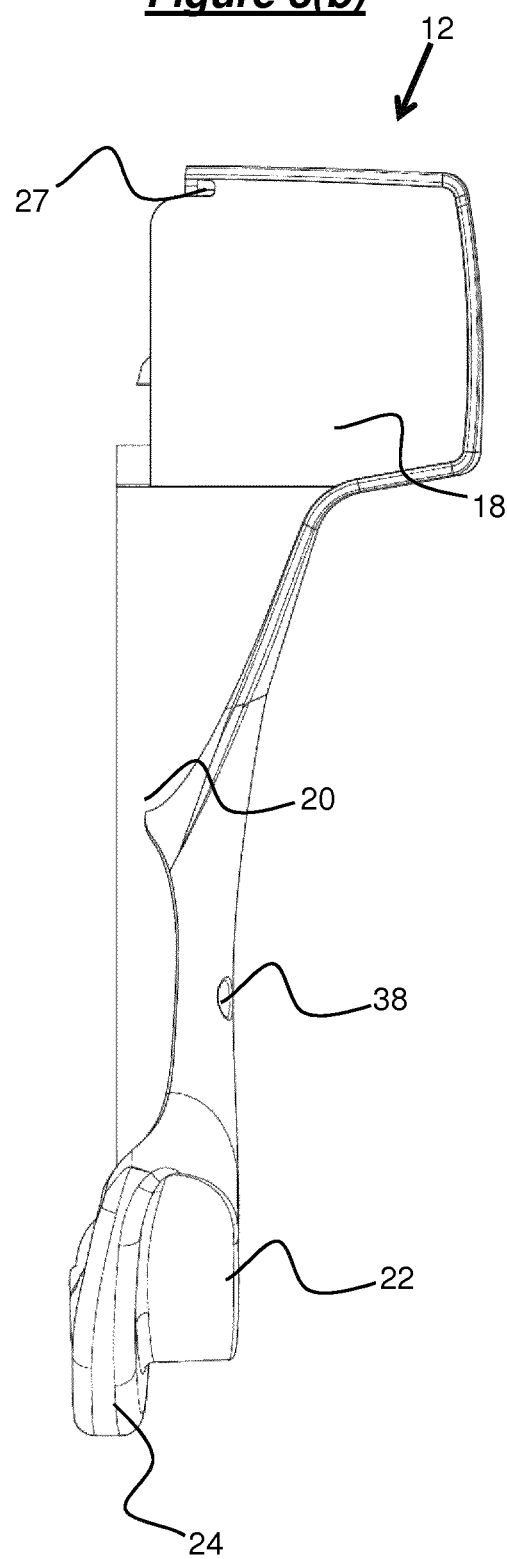

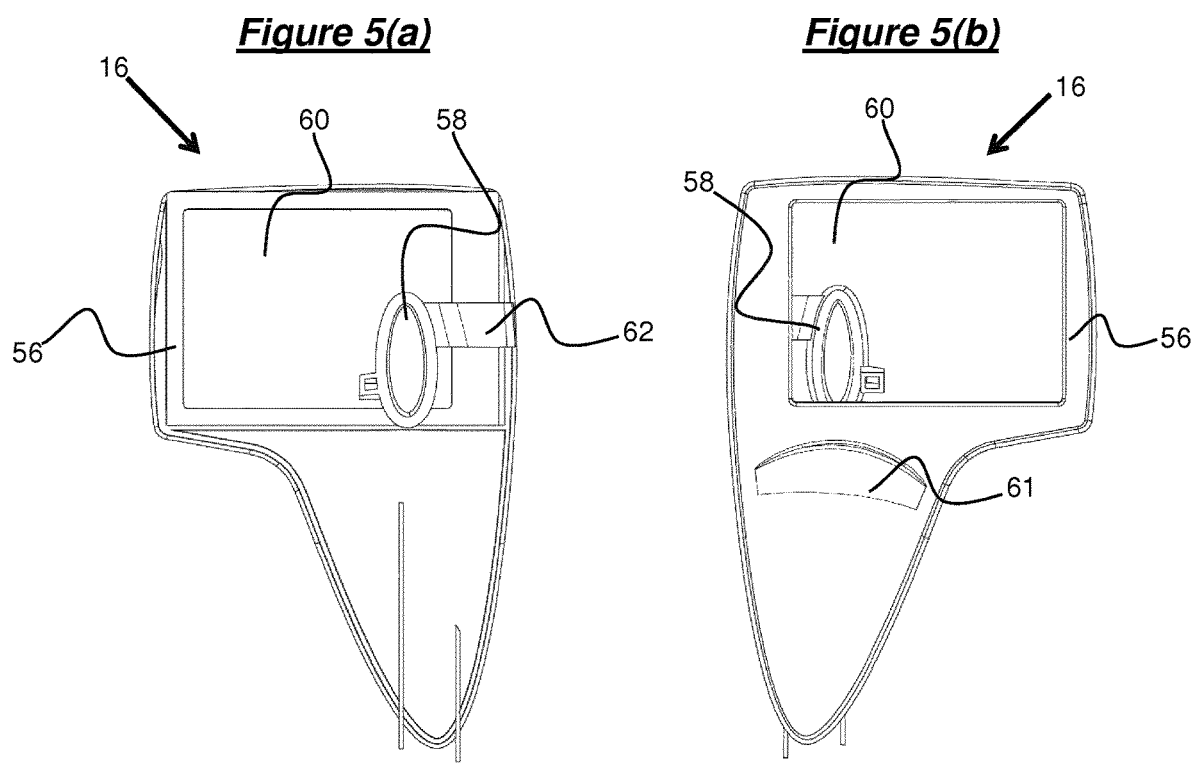

VIDEO LARYNGOSCOPES

This application is a national stage application under 35 U.S.C. § 371 of PCT Application No. PCT/EP2016/061015, filed May 17, 2016, which claims the priority benefit of Great Britain Application No. 1508739.8, filed May 21, 2015, which are hereby incorporated by reference in their entirety.

The present invention relates to laryngoscopes, and in particular to laryngoscopes having a video camera component.

Typically, laryngoscopes have a handle and an interchangeable blade, which may be provided in a range of shapes and sizes to accommodate a range of patients. Historically, handles and blades have been reusable, such that those components can be sterilised between successive uses. However, there is a general trend towards disposable products to reduce the risk of infection within medical facilities. It is known in the prior art to provide single-use laryngoscopes, yet the shift towards disposable laryngoscopes requires closer control of manufacturing costs in order to provide a viable, ongoing solution for a medical facility or organisation. Accordingly, certain functional attributes of a disposable product can become compromised in order to accommodate a simple and cost effective product design.

Conventional laryngoscopes are used, for example, during tracheal intubation of a patient. A common method of intubation requires the insertion of an endotracheal tube through the mouth of a patient into the trachea. Orotracheal intubation may be required, for example, when it is necessary to mechanically ventilate a patient. It is common practice to use a laryngoscope as a visual aid during intubation. However, conventional laryngoscopes require a direct line of sight between an operator and a patient's trachea, which may be difficult to achieve during use. Furthermore, the glottis and/or epiglottis of a patient may obstruct the vision of the operator of the laryngoscope during use.

It is known in the prior art to utilise laryngoscopes having optical arrangements to allow an operator to obtain a clear view during tracheal intubation. In particular, it is known to incorporate a video camera into the blade of a laryngoscope, and to transmit images from the camera to a display which may be viewed during the intubation procedure. Such a display may be either remote from, or attached to, the laryngoscope.

Where displays are attached to the laryngoscope, the displays are often bulky, and extend outwardly from the body of the laryngoscope, making the laryngoscope unwieldy, and further posing an obstruction to the direct line of sight of an operator, should this be required. Furthermore, such displays are typically expensive, and are generally therefore components that may be sterilised and reused after each intubation procedure. This may lead to an increased risk of infection within medical facilities, and the need for a removable mounting between the display and the laryngoscope may generally increase the cost of manufacture of the device.

There have now been devised improved laryngoscopes which overcome or substantially mitigate the aforementioned and/or other disadvantages associate with the prior art.

According to a first aspect of the present invention there is provided a laryngoscope comprising a body including a handle for receiving a palm of a user's hand, in use, a laryngoscope blade extending from a distal end of the body, and a display screen housing extending from a proximal end of the body, the display screen housing accommodating a display screen component, and a grip portion being provided for receiving at least a thumb and index finger of the user's hand, in use, the grip portion being located intermediate the display screen component and the handle.

The laryngoscope according to the first aspect of the present invention is advantageous principally in the provision of a display screen housing extending from a proximal end of the body, and a grip portion for receiving at least a thumb and index finger of the user's hand, which is located intermediate the display screen component and the handle. In particular, the present invention may provide a compact, inexpensive device, which may be suitable for use as a disposable device, and which provides a user with a balanced grip offering improved maneuverability relative to prior art devices intended to be compact, inexpensive devices.

The grip portion may be defined by portions of the body and/or portions of the display screen housing of the laryngoscope. The grip portion may comprise external surfaces of the laryngoscope, which may extend circumferentially about the laryngoscope, between the display screen component and the handle. The grip portion may be tapered such that the grip portion decreases in width between the display screen component and the handle. Thus the grip portion may provide an ergonomically shaped surface for receiving a user's grip.

A thumb-receiving surface of the grip portion may be shaped and/or dimensioned to receive at least a portion of a thumb of a user, in use, for example the thumb-receiving surface of the grip portion may be contacted by at least a portion of the thumb. The at least a portion of the thumb that is received by the thumb-receiving surface of the grip portion may be a pad of the thumb, eg the distal pad of the thumb.

For increased control, the handle and the grip portion may be arranged such that the thumb extends substantially parallel to a longitudinal axis of the laryngoscope, eg a longitudinal axis that extends between the proximal and distal ends of the body of the laryngoscope, substantially parallel to a medial plane substantially bisecting the body and the blade of the laryngoscope. The handle and the grip portion may be arranged such that the distal pad of the thumb contacts the thumb-receiving surface of the grip portion, and is orientated substantially orthogonally relative to the direction of extension of the blade. The thumb may also be at full extension when contacting the thumb-receiving surface of the grip portion.

The thumb-receiving surface may be a surface that faces a user, in use, and hence may face in a direction that is opposite to the direction of extension of the blade. The thumb-receiving surface may be substantially flat, or at least partially curved, eg concave in one or more axes. The thumb-receiving surface may have a width that is at least equal to, and preferably wider than, the width of a thumb of a user, eg at least 50% or 100% wider than the width of a thumb of a user.

The thumb-receiving surface of the grip portion may comprise a location formation for engagement by at least a portion of a thumb of a user. The location formation may be adapted to impede longitudinal movement of a thumb of a user along the thumb-receiving surface in at least one direction. The location formation may be adapted to impede longitudinal movement of a thumb of a user toward the display screen component. The location formation may comprise an abutment surface for contacting at least a portion of a thumb, or a tip of a thumb, of a user, in use. The location formation may, for example, take the form of an upstanding projection, or ridge, or rib, or the like.

The abutment surface may have a width that is substantially equal to, or preferably greater than, the width of a tip of a thumb of a user, and may have a shape that also impedes transverse movement of the thumb. The abutment surface may have outer regions that extend at least partially backwards relative to the tip of the thumb, towards the user's hand. For example, the abutment surface may be curved along its length, eg in the form of an arc.

The location formation may at least partially define an enclosure which may accommodate at least a portion of a thumb of a user in use. The location formation may be integrally formed with the grip portion.

A finger-receiving surface of the grip portion may be shaped and/or dimensioned to receive at least a portion of at least one finger of a user in use. The finger-receiving surface may be shaped and/or dimensioned to receive at least a portion of up to two fingers, eg the index and middle fingers, or preferably only one finger, eg the index finger, of a user. The remainder of the fingers (other than the thumb) may be located on the handle of the laryngoscope, in use.

The finger-receiving surface may include a surface that faces away from a user, in use, and hence may include a surface that faces in a direction that is in substantially the same direction as the direction of extension of the blade. This surface may face in an opposite direction to the thumb-receiving surface described above. This surface may be contacted by an intermediate portion of a finger, eg the portion of the finger corresponding to the intermediate phalanx. In this configuration, the portions of the finger corresponding to the proximal phalanx and the distal phalanx may contact the side surfaces of the grip portion, which may be substantially parallel to a medial plane substantially bisecting the body and the blade of the laryngoscope The finger-receiving surface may comprise a location formation for engagement by at least a portion of a finger of a user. The location formation may be adapted to impede movement of a finger of a user, eg towards the display screen component and/or towards the handle. The location formation may be adapted to impede movement of a finger of a user towards the display screen component and the handle. The location formation may comprise an abutment surface for contacting at least a portion of a finger, or one or both sides of a finger, of a user, in use. The location formation may, for example, take the form of an upstanding projection, or ridge, or rib, or the like.

The finger-receiving surface may be bounded on at least one side, and preferably both sides, by a location formation. The finger-receiving surface may be recessed or depressed relative to the location formations. The finger-receiving surface may therefore comprise a recess or depression for receiving at least a portion of at least one finger of a user. The recess or depression may be bounded on at least one side, and preferably both sides, by a lip or upstanding projection, which forms a location formation. The lip or upstanding projection(s) may extend transversely across the grip portion, relative to a medial plane substantially bisecting the body and the blade of the laryngoscope. The recess or depression, and lip or upstanding projection(s), may thereby at least partially define an enclosure for receiving at least a portion of at least one finger of a user.

The grip portion may be adapted to facilitate grasping of the laryngoscope by a user. The grip portion may be adapted to increase frictional contact between the hand of a user and the laryngoscope.

The grip portion may be formed from the same material as the remainder of the body and/or the display screen housing of the laryngoscope. Thus, the laryngoscope may comprise components that define the grip portion, the body and the display screen housing. Alternatively, the grip portion may comprise a different material to the remainder of the body and/or the display screen housing of the laryngoscope. In such circumstances, the laryngoscope may comprise components that define the grip portion, the body and the display screen housing that are singular composite structures, and may be formed as part of a single moulding process. The moulding process used for formation of the composite components may be a two-shot injection moulding process or an overmoulding process.

The grip portion may comprise a material that is relatively soft or compliant relative to the remainder of the body and/or the display screen housing of the laryngoscope. The grip portion may comprise a material that has a higher coefficient of friction than the remainder of the body and/or the display screen housing of the laryngoscope. The grip portion may comprise a rough or textured surface, which may, for example, take the form of a plurality of upstanding projections and/or recesses disposed upon the grip portion. The rough or textured surface may be formed of the same material as the remainder of the body and/or the display screen housing of the laryngoscope, or may be formed of a different material to the remainder of the body and/or display screen housing of the laryngoscope. The grip portion may be movable relative to the handle and/or the display screen component, and may be fixable in different positions, such that a user can locate the grip portion in a desired position, intermediate the display screen component and the handle.

The handle portion may be elongate in form, and may have a generally cylindrical or frusto-conical shape. The handle may have a profile that is at least partially curved, and preferably ergonomically contoured to receive a palm of a user's hand, in use, and one or more associated fingers. The handle may be substantially hollow in nature.

The display screen housing may be formed integrally with at least the body of the laryngoscope. The display screen housing and/or the display screen component may be non-removable from the body of the laryngoscope, eg without disassembling or breaking the body of the laryngoscope. The laryngoscope may comprise at least one housing component that defines a portion of the body of the laryngoscope and a portion of the display screen housing of the laryngoscope. This configuration reduces manufacturing costs relative to laryngoscopes with removable display screen assemblies.

The laryngoscope blade may be over-moulded onto the body, for example as part of a two-shot injection moulding process. The blade may be fixedly attached to the body. For example, the blade may be attached to the body via a fastener such as a screw or the like. Alternatively, the blade may be clamped by the plurality of housing components, such that the housing components act to retain the blade in position. The blade may comprise at least one reinforced region. The reinforced region may comprise a metallic material. The blade may be formed of metal, or of plastics, or of a combination thereof.

A configuration has been devised in which the laryngoscope may comprise at least one unitary housing component that defines a portion of the display screen housing of the laryngoscope, a portion of the body of the laryngoscope, and a portion of the blade of the laryngoscope. This configuration offers significant advantages relative to prior art, providing a robust assembly that is inexpensive to manufacture, and which may be suitable for use as a disposable device.

Thus, according to a second aspect of the present invention, there is provided a laryngoscope comprising a body, a laryngoscope blade extending from a distal end of the body, and a display screen housing extending from a proximal end of the body, wherein the laryngoscope comprises at least one unitary housing component that defines at least a portion of each of the body, the laryngoscope blade and the display screen housing.

The laryngoscope according to the second aspect of the present invention is advantageous principally as the laryngoscope comprises at least one unitary housing component that defines at least a portion of each of the body, the laryngoscope blade and the display screen housing. This configuration offers significant advantages relative to prior art, providing a robust assembly, using a reduced number of components, that is inexpensive to manufacture, and which may be suitable for use as a disposable device. A disposable laryngoscope, ie a laryngoscope that may be thrown away after a single use, may eliminate the risk of contamination that is associated with multiple use devices. Furthermore, the unitary configuration may reduce points of weakness associated with the construction (eg points of weakness located in the region of joints between separate components), and, when partnered with the use of high strength materials (for example reinforced plastics or glass filled PPS) to form the body, the laryngoscope blade, and the display screen housing, may provide a particularly robust configuration.

The laryngoscope may comprise two or more unitary housing components, at least one of which at least partially defines each of the display screen housing, the body of the laryngoscope, and the laryngoscope blade. The laryngoscope may comprise any number of unitary housing components, any number of which may at least partially define each of the display screen housing, the body of the laryngoscope, and the laryngoscope blade. The plurality of housing components may be shaped and dimensioned to have corresponding engagement formations, such that the housing components may be brought together into engagement. The housing components may be fastened together, for example by corresponding formations of the housing components that are adapted to fasten to each other, eg a snap-fit arrangement, or by separate fastener components, eg screws or the like. The housing components may be releasable from each other but, in preferred embodiments, the housing components are permanently fixed together.

The housing components may be brought together to encapsulate the display screen component of the display screen housing. The housing components may define an opening, through which a display screen of the display screen component is visible. The opening may be defined by an aperture in a single housing component, eg a rear housing component, or may be defined by aperture portions of two or more housing components. The display screen component may be arranged with a display screen extending at least partially, or entirely, across the opening defined by the housing components.

The laryngoscope may comprise at least two unitary housing components, a first housing component that defines at least a portion of each of the body, the laryngoscope blade and the display screen housing, and a second housing component that defines at least a portion of the body and the display screen housing. In presently preferred embodiments, the second housing component also defines at least a portion of the laryngoscope blade, such that the laryngoscope blade is defined by at least the first and second housing components.

The laryngoscope may comprise at least two side housing components, which at least partially define each side of the body and display screen housing of the laryngoscope, relative to a medial plane bisecting the body and the laryngoscope blade. The laryngoscope may also comprise a rear housing component, which defines an opening through which the display screen of the display screen component is visible. For example, the rear housing component may surround the exposed surface of the display screen component. In presently preferred embodiments, the laryngoscope comprises first and second side housing components, and an interposed rear housing component. These housing components may be the only components, other than the display screen component, that define the exterior of the display screen housing and/or the body of the laryngoscope.

The rear housing component may partially, or substantially, define the thumb-receiving portion of the grip portion described above, and may also include the associated location formation. At least one of the side housing components may define the finger-receiving portion of the grip portion described above, and may also include the associated location formation(s).

The housing component(s) may be formed of a plastics material, and may be formed by injection moulding. The housing components may be adapted to house electronic components, for example the housing components may at least partially define an internal cavity for accommodating electronic components. An interior surface of at least one of the housing components may comprise retaining formations for retaining electronic components within an internal cavity.

The one or more housing components may be shaped to define an aperture for receiving a switch, eg a depressible button, for the activation of electronic components. The aperture may be formed in a single housing component, or two or more housing components may comprise corresponding aperture portions, which may combine to define an aperture for receiving a switch.

The laryngoscope may comprise a camera, which may send image signals to the display screen component. The camera may be adapted to capture still images and/or video sequence images. The camera may therefore be a video camera. The camera may be shaped and dimensioned to be received in the laryngoscope blade.

The camera is preferably housed within the interior of the laryngoscope blade, acting through an opening in the laryngoscope blade. For example, the lens of the camera may be housed in an aperture in the laryngoscope blade. The camera may be located in a region proximate a tip of the laryngoscope blade. The camera may be located upon an interior surface of the laryngoscope blade. The laryngoscope blade may comprise a camera housing portion, which may extend longitudinally along the laryngoscope blade. The camera housing portion may be substantially hollow, such that the camera housing portion is in communication with a hollow interior of the laryngoscope. The camera housing portion may have a curved profile, so as to conform to the laryngeal passage of a patient, and may define part of a guide for an endotracheal tube.

The laryngoscope blade may comprise a blade portion and a camera housing portion, which are arranged to form an L-shaped guide, eg for endotracheal tubes. The laryngoscope blade may be defined by at least the first and second housing components. The blade portion may be substantially defined by the first housing component, and the camera housing portion may be substantially defined by the first and second housing components. For example, the first and second housing components may cooperate to define the camera housing portion, eg including an interior chamber for accommodating the camera.

The laryngoscope blade may extend outwardly from the body of the laryngoscope, such that the laryngoscope blade extends substantially orthogonally to the body. The transition between the body and the laryngoscope blade may be curved, and thus may at least partially prevent damage to the laryngeal passage of a patient during use. The transition between the body and the laryngoscope blade may be smooth, for example in the form of an arc that extends through at least 45°, at least 60°, eg around 90°. The laryngoscope blade is preferably curved along its length so as to facilitate insertion of the laryngoscope blade into the laryngeal passage of a patient in use.

The laryngoscope blade may be curved along its length, such that a distal portion of the laryngoscope blade curves towards the body. The laryngoscope blade may comprise a free end having a tip. The tip of the free end may have a rounded profile.

The display screen component may have a display screen, which may have an orientation, pixel size and/or colour capability to match the user requirements. The display screen may be adjustable in one or more of these aspects or, in presently preferred embodiment, the display screen is not adjustable and hence has a fixed configuration. In presently preferred embodiments, the display screen has a landscape orientation, such that its major axis is substantially orthogonal to a medial plane substantially bisecting the body and the blade of the laryngoscope. The display screen may have a width that is between 5 cm and 15 cm, or between 7 cm and 13 cm. The display screen may have a height that is between 3 cm and 13 cm, or between 5 cm and 11 cm. The display screen may be greyscale.

The display screen component may comprise an LCD display screen, or may comprise any other type of appropriate display screen. The display screen may be flexible. The display screen may have touch-screen capabilities. The display screen may be connected to the camera, for example via a wired connection, or via a circuit board. The display screen and the camera may be mounted on a flexible circuit board, which may remove the need for expensive connectors between these components. The display screen may be remotely connected to the camera via a wireless connection, including, but not limited to, a radio connection, for example a 2.4 GHz radio connection.

The laryngoscope may comprise an electronic memory for storing images captured by the camera. The memory may be any appropriate electronic memory, for example in the form of a non-removable chip or in the form of a removable device, eg a memory card, such as an SD card, micro SD card, or the like. The electronic memory may be non-volatile memory. In presently preferred embodiments, the electronic memory is flash memory.

The electronic memory may be preinstalled in the laryngoscope, or may be insertable by a user. The electronic memory may be removable from the laryngoscope. The electronic memory may include a label for identifying a patient. For example, the label may take the form of a surface, upon which a patient indicator, eg a name or number, may be written in ink. The label may be graspable by a user so as to remove the electronic memory from the laryngoscope when the label is pulled by a user. The label may project outwardly from the laryngoscope, thereby allowing the label to be graspable by a user. The label may be flexible.

The laryngoscope may comprise a microcontroller. The microcontroller may be used to initialise the camera and/or the display screen component. In preferred embodiments, the microcontroller may solely be used to initialise the camera and the display screen component, and may be configured not to process any of the data transferred between the camera and the display screen component, in use. Such limited functionality of the microcontroller reduces the requirements imposed on the microcontroller, and thus a less expensive microcontroller may be used than those that are conventionally used in the prior art. The less expensive microcontroller that is required for the present invention may facilitate manufacture of a single-use, disposable laryngoscope. The microcontroller may solely be used to initialise the camera and the display screen component where the transmission distance between the camera and the display screen component is small, for example less than, or equal to, 300 mm.

Thus, according to a third aspect of the present invention there is provided a laryngoscope comprising a display screen component, a camera for transmitting images to the display screen component, and a microcontroller configured to initialise the display screen component and/or the camera, wherein the microcontroller is configured not to process any of the data transferred between the camera and the display screen component, in use.

The laryngoscope according to the third aspect of the present invention is advantageous principally in the microcontroller being configured to initialise the display screen component and/or the camera, but not to process any of the data transferred between the camera and the display screen component, in use. This enables the display screen component and the camera to cooperate with each other, without the need for any processing of the image data by the microcontroller. The less expensive microcontroller that is required for the present invention may facilitate manufacture of a single-use, disposable laryngoscope.

The initialisation of the display screen may comprise the microcontroller providing information to the display screen regarding power control settings for the display screen, the form of the input signal that will be received from the camera, the format of the image data, and/or the form of the interface between the microcontroller and the display screen component. The information regarding the form of the input signal and/or the image data that will be received from the camera may include information regarding orientation, size, colour, pixel arrangement, image correction, eg gamma correction, and overall image data format.

The initialisation of the camera may comprise the microcontroller providing information to the camera regarding power control settings for the camera, lens settings for the camera, the form of the output signal that will be provided to the display screen, the format of the image data and any image processing by the camera, and/or the form of the interface between the microcontroller and the camera. The information regarding the form of the output signal and/or the image data that will be provided to the camera may include information regarding orientation, size, colour, pixel arrangement, image correction, and overall image data format.

The display screen and the camera may be adapted, for example during initialisation, to be supplied by the same input voltage, thereby enabling less regulators to be used.

In presently preferred embodiments, the image data supplied by the camera to the display screen has a scale between 320×240 and 640×480, and the data format is RGB, eg RGB565.

It will be recognised that preferable features of each of the aspects of the present invention may be equally applied to other aspects of the present invention where appropriate.

Practicable embodiments of the invention are described in further detail below with reference to the accompanying drawings, of which:

FIG. 3(a) is a front view of a first housing portion of the laryngoscope of FIG. 1;

FIG. 3(b) is a rear view of the first housing portion of FIG. 3(a);

FIG. 5(a) is a front view of a third housing portion of the laryngoscope of FIG. 1;

FIG. 5(b) is a rear view of the third housing portion of FIG. 5(a);

Although the terms "upper", "lower", "rear", "front" and the like are used in the description of the invention below with reference to the figures, it will be appreciated that the invention is not limited to any specific orientation and, indeed, the orientation of the video laryngoscope may change during use. Accordingly, those terms should be construed as being relative terms only with respect to the other features of the video laryngoscope within a common frame of reference.

Figure 1:
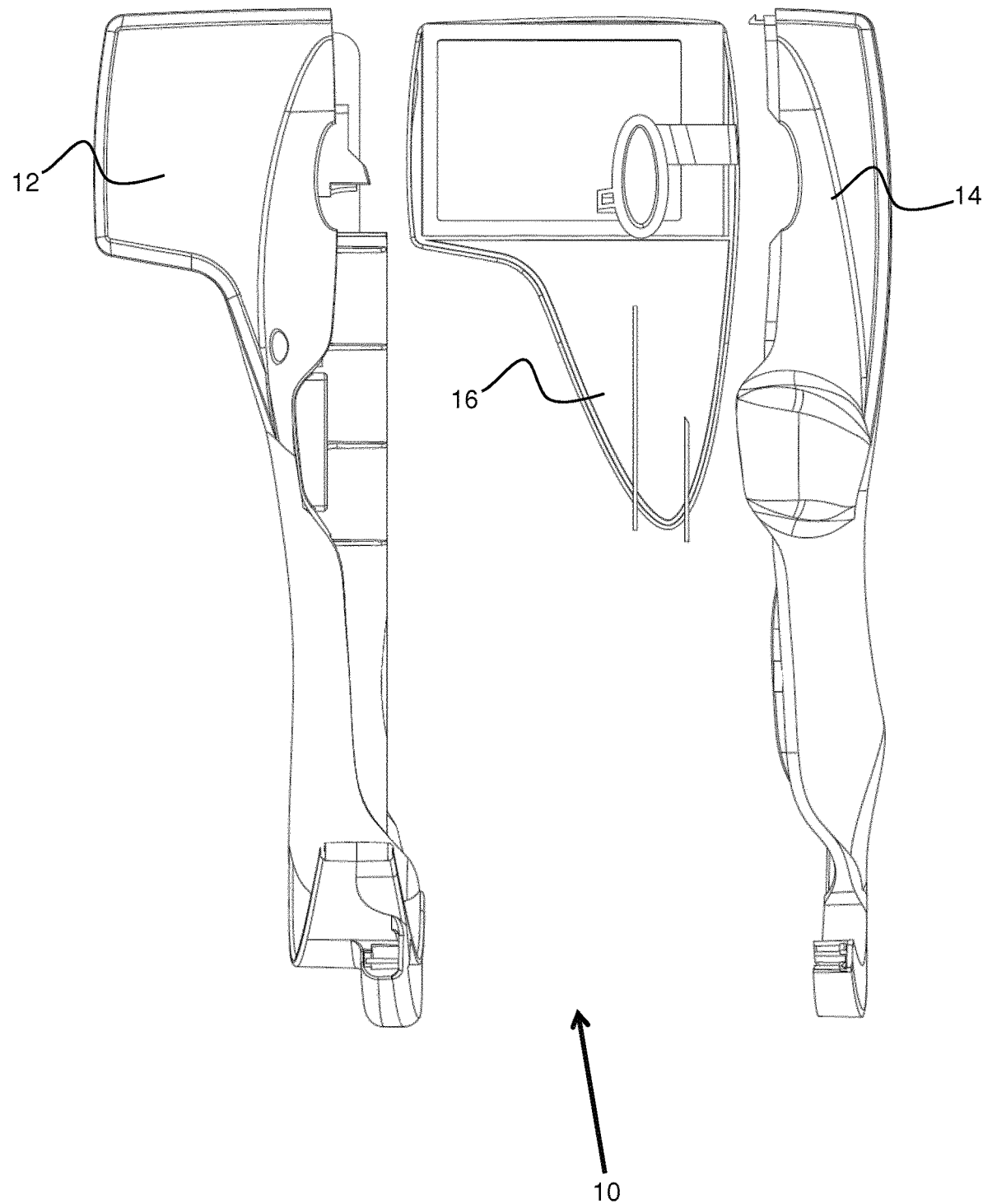
FIG. 1 is an exploded front view of a video laryngoscope according to a first aspect of the present invention.
Figure 2:
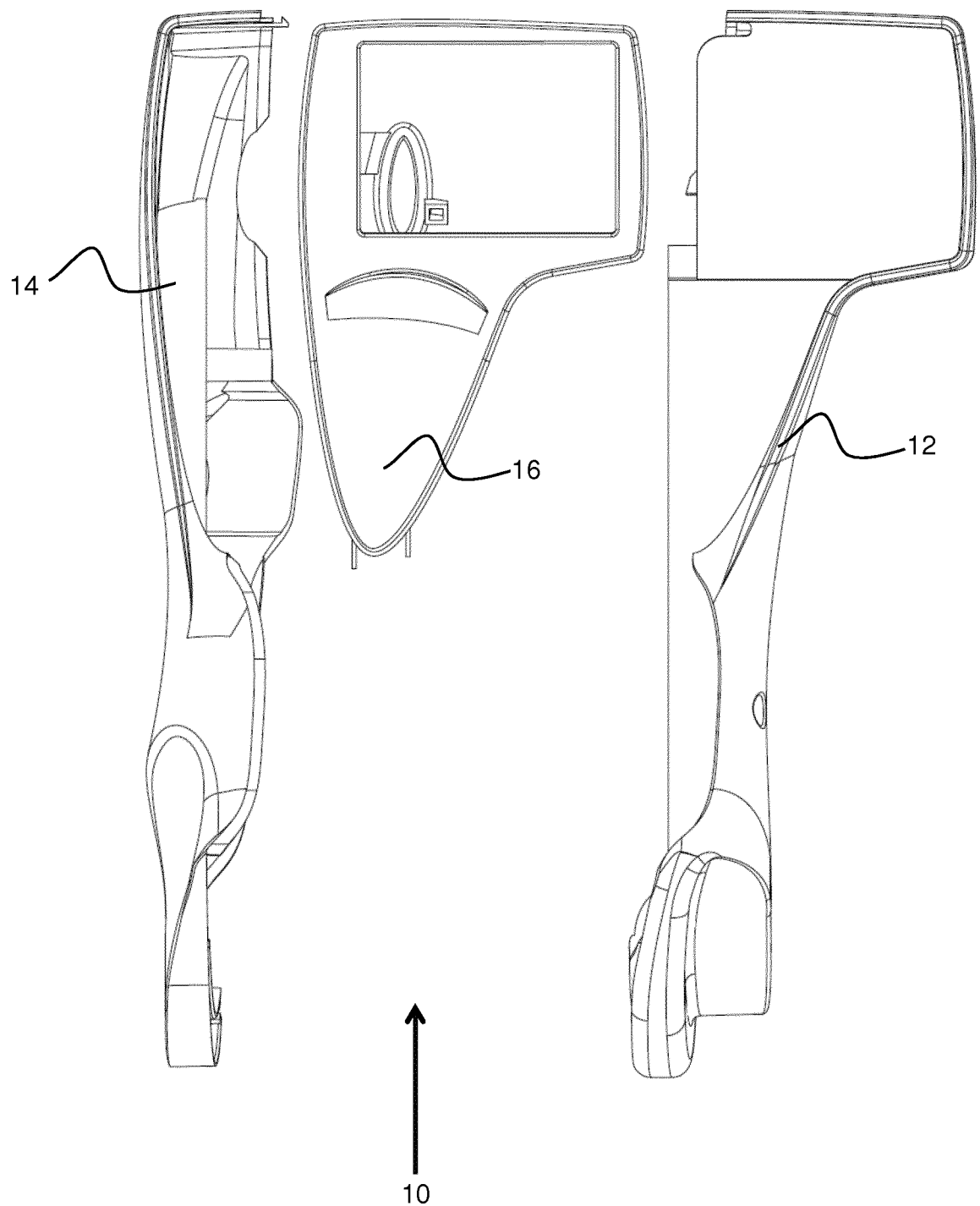
FIG. 2 is an exploded rear view of the laryngoscope of FIG. 1.
Figure 6:
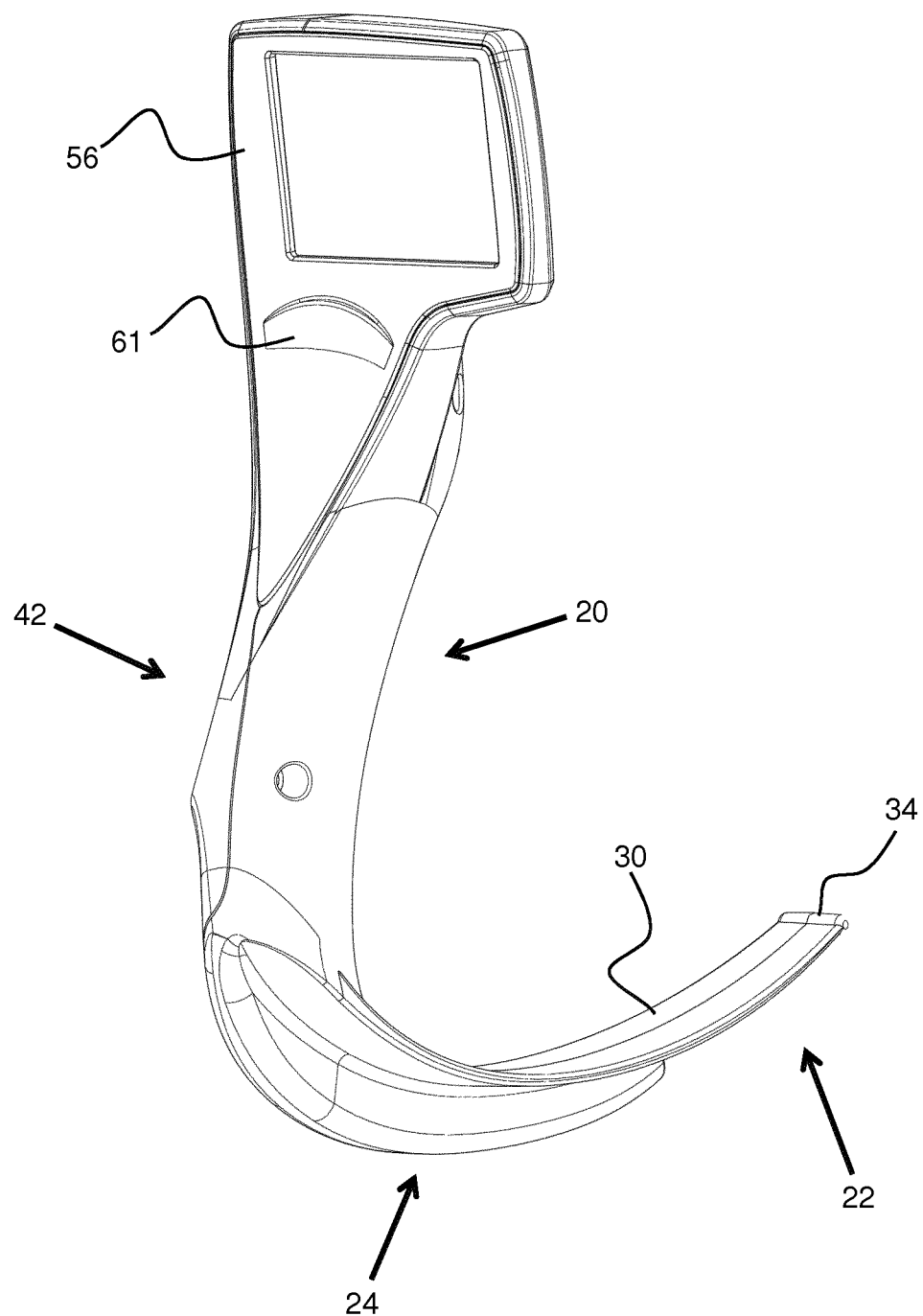
FIG. 6 is a rear perspective view of the laryngoscope of FIG. 1 in an assembled configuration.
Figure 7:
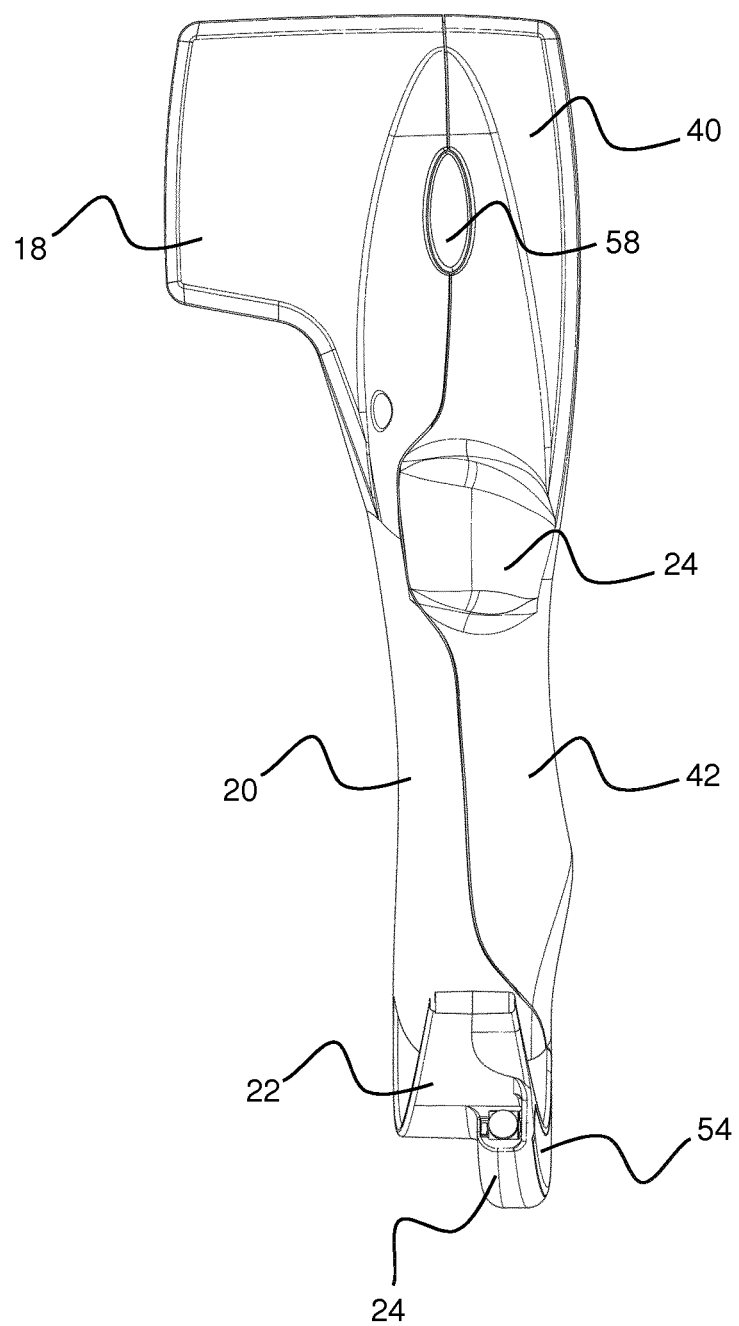
FIG. 7 is a front view of the laryngoscope of FIG. 6.
Figure 8:
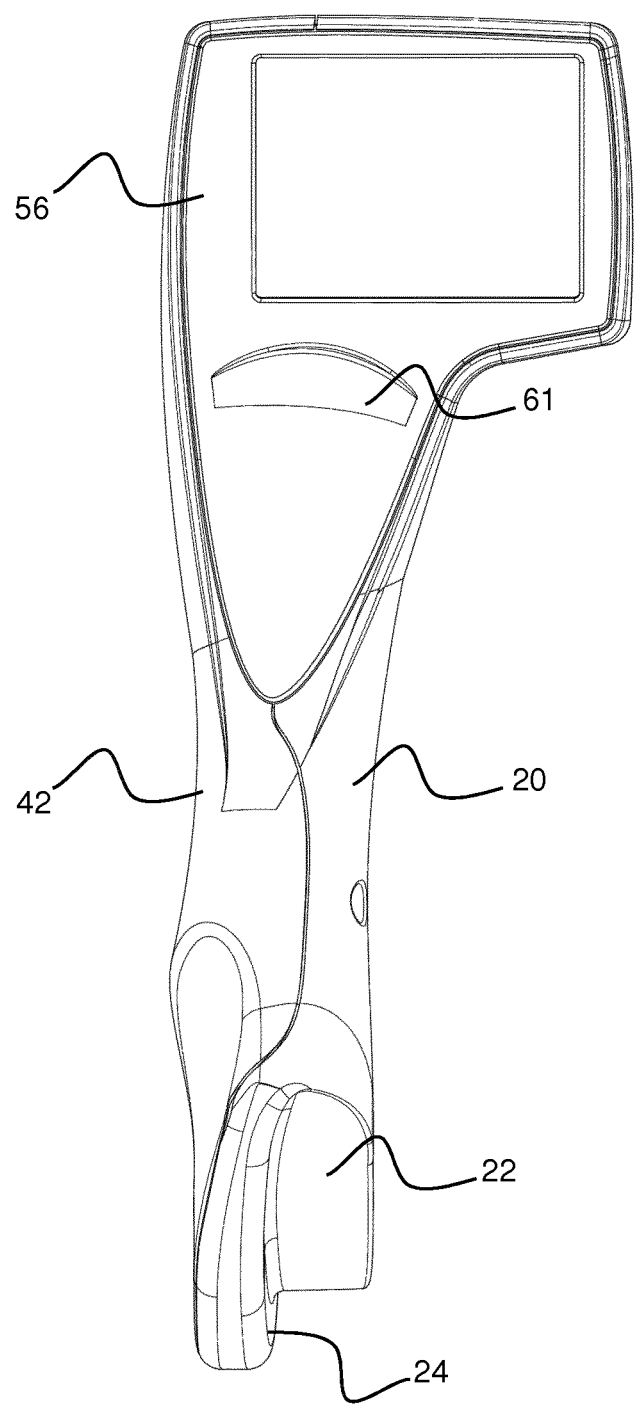
FIG. 8 is a rear view of the laryngoscope of FIG. 8.

A laryngoscope according to the present invention, generally designated 10, is shown in an exploded configuration in FIGS. 1-2, and in a fully assembled configuration in FIGS. 6-8. The laryngoscope 10 comprises first 12, second 14, and third 16, housing components, which when assembled form a unitary laryngoscope housing.

The first housing component 12 is shown in isolation in FIGS. 3(a) and 3(b), and comprises a display housing portion 18 for housing a display of the laryngoscope, a body portion 20 which may be grasped by a user, a blade portion 22 for insertion into a patient's trachea, and a camera housing portion 24 for housing a camera and/or light. The first housing component 12 further comprises a plurality of apertures 38 for receiving corresponding fasteners, for example screws or the like.

The display housing portion 18 is located at an upper end of the first housing component 12, and has a substantially rectangular profile. The display housing portion 18 is substantially hollow, with an open face on one side, which has a peripheral edge shaped and dimensioned to receive a corresponding portion 40 of the second housing component 14 when the laryngoscope 10 has been assembled. The display housing portion 18 also has an open rear face that is further shaped and dimensioned to engage a corresponding portion of the third housing component 16 when the laryngoscope 10 is assembled.

A region of a front face of the display housing portion 18 comprises a cut-away 26, which is substantially hemi-elliptical in form. The cut-away 26 is shaped and dimensioned to receive at least a portion of a switch button 58 when the laryngoscope 10 is assembled. An upper region of the rear face of the display housing portion 18 comprises a recess 27 for engaging a corresponding projection 46 of the second housing component 14.

The body portion 20 is integrally formed with, and depends downwardly from, the display housing portion 18. The body portion 20 is substantially elongate in form, and has a curved profile so as to conform to the hand of a user in use. The body portion 20 is substantially hollow in nature, and at least an upper region of the rear surface of the body portion 20 is shaped and dimensioned to receive a corresponding region of the third housing component 16 when the laryngoscope 10 is assembled. The body portion 20 has an open face on one side, with a peripheral edge that is shaped and dimensioned so as to engage a corresponding portion of the second housing component 14 when the laryngoscope 10 is assembled. An upper region of the front face of the body portion 20 comprises a cut-away 28, which is shaped and dimensioned to receive a corresponding grip portion 50 of the second housing component 14 when the laryngoscope 10 is assembled.

The display housing portion 18 and the body portion 20 are oriented such that part of the display housing portion 18 extends laterally outwardly from the upper region of the body portion 20 at a substantially orthogonal angle.

The blade portion 22 is integrally formed with, and extends outwardly from, a lower region of the body portion 20. The blade portion 22 extends outwardly from the body portion 20 in a substantially forward direction, and is curved along its length such that an upper surface 30 of the blade faces towards the body portion 20. The blade portion 22 further comprises a lower surface 32 which also curves towards the free end 34 of the blade portion 22, such that the upper 30 and lower 32 surfaces converge in the vicinity of the blade tip 34. The blade tip 34 comprises a lip formation which is generally rounded or blunt. The blade portion 22 is further tapered along its width, such that the blade tip 34 is narrower than the interface between the blade portion 22 and the body portion 20.

The camera housing portion 24 is substantially hollow in form, is integrally formed with each of the body portion 20 and the blade portion 22, and extends along the lower surface 32 of the blade portion 22 from a proximal end at the body portion 20 towards the blade tip 34. The camera housing portion 24 has a rounded-arch shaped profile, and a lower region of the camera housing portion 24 comprises a recess 36 shaped and dimensioned to receive a corresponding portion 44 of the second housing component 14. The hollow interior of the camera housing portion 24 is in fluid communication with the hollow interior of the body portion 20, thus allowing a camera and associated electronics to be held within the camera housing portion 24 and the body portion 20. The tip 37 of the camera housing portion is open, such that an unobstructed view is presented to a camera housed within the laryngoscope 10.

Figure 4A:
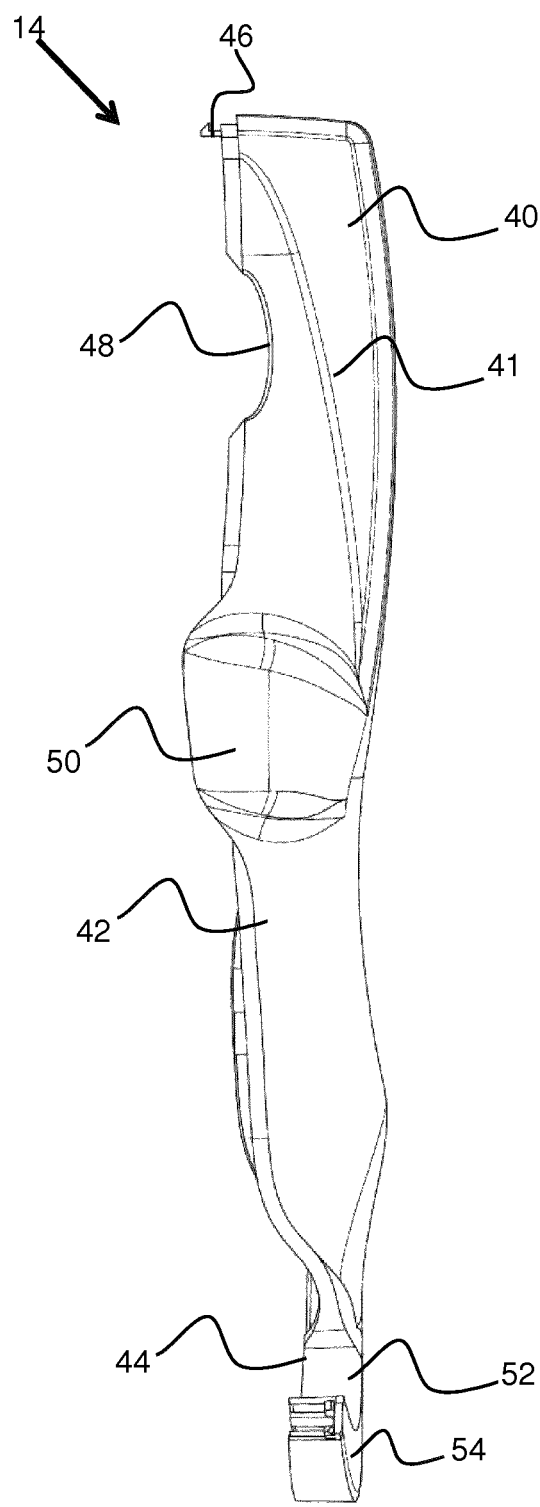
FIG. 4(a) is a front view of a second housing portion of the laryngoscope of FIG. 1.
Figure 4B:
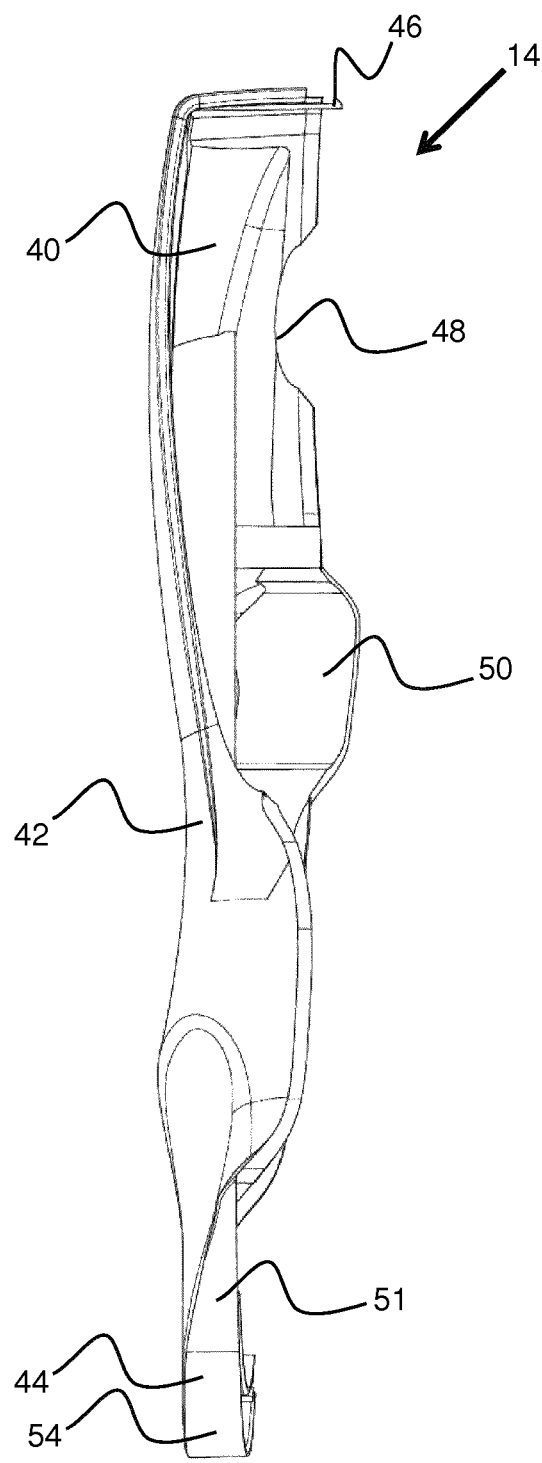
FIG. 4(b) is a rear view of the second housing portion of FIG. 4(a)

The second housing component 14 is shown in isolation in FIGS. 4(a) and 4(b), and comprises a display housing portion 40 for housing a display of the video laryngoscope, a body portion 42 which may be grasped by a user, and a camera housing portion 44 for housing a camera and/or light.

The display housing portion 40 is located at an upper end of the second housing component 14, and a front face 41 of the display housing portion 40 has a substantially rectangular profile. The display housing portion 40 of the second housing component 14 has a reduced width relative to the display housing portion 18 of the first housing component 12, and thus appears more elongate in form. The display housing portion 40 is substantially hollow, with an open face on one side, and a further open rear face, with peripheral edges that are shaped and dimensioned to receive corresponding portions of the third housing component 16 when the laryngoscope 10 has been assembled. The open face on one side of the second housing component 14 is further shaped and dimensioned to engage a corresponding portion 18 of the first housing component 12 when the laryngoscope 10 is assembled.

An uppermost region of the display housing portion 40 comprises a laterally extending projection 46 for engaging a corresponding recess 27 of the display portion 18 of the first housing component 12, with a snap fit. A region of a front face of the display housing component 40 comprises a cut-away 48, which is substantially hemi-elliptical in form. The cut-away 48 is shaped and dimensioned to receive at least a portion of a switch button 58 when the laryngoscope 10 is assembled. When the laryngoscope 10 is assembled, the cut-away 26, and the cut-away 48, correspond to surround substantially the entirety of the perimeter of the switch button 58.

The body portion 42 is integrally formed with, and depends downwardly from, the display housing portion 40. The body portion 42 is substantially elongate in form, and has a curved profile so as to conform to the hand of a user in use. The body portion 42 is substantially hollow in nature, and at least an upper region of the body portion 42 is shaped and dimensioned to receive a corresponding region of the third housing component 16 when the laryngoscope 10 is assembled. The body portion 42 has an open face on one side that is shaped and dimensioned so as to engage a corresponding portion of the first housing component 12 when the laryngoscope 10 is assembled. An upper region of the front face of the body portion 42 comprises a grip portion 50, which is shaped and dimensioned to be received within the corresponding cut-away 28 of the first housing component 12 when the laryngoscope is assembled.

The grip portion 50 takes the form of an upstanding formation on the front face of the body portion 42, and is integrally formed with the body portion 42. The upstanding formation is raised from the body portion 42, such that the upstanding formation has the global form of a bump or ridge or the like. A front surface of the grip portion 50 is contoured, with the contoured surface being shaped and dimensioned to receive an index finger of a user, in use. The contoured surface comprises upper and lower ridges, between which a generally recessed surface is provided. The upper and lower ridges extend transversely across the grip portion 50, and may thereby prevent longitudinal movement of the index finger of user in use. The side edges of the contoured surface are free from any projections, in order to provide comfortable location of the index finger of a user.

The camera housing portion 44 is integrally formed with, and depends downwardly from, a lower region of the body portion 42. An upper region 51 of the camera housing portion is curved along its length, and a lower region 54 of the camera housing portion 44 is substantially hollow in form, and is curved along its length. The lower region 54 extends outwardly from the upper region 51 in a substantially forward direction, such that an upper surface 52 of the lower region 54 faces towards the body portion 42. The lower region 54 comprises an open face on one side that is shaped and dimensioned to engage a corresponding region of the first housing component 12 when the laryngoscope is assembled. The lower region 54 is shaped and dimensioned so as to be received within the recess 36 of the camera housing portion 24 of the first housing component 12, such that a camera is encapsulated by the camera housing portions 24,44 when the laryngoscope 10 is assembled.

The third housing component 16 is shown in isolation in FIGS. 5(*a*) and 5(*b*), and comprises a screen receiving portion 56 and a switch button 58 for activation of the laryngoscope 10. An upper region of the screen receiving portion 56 has a substantially rectangular profile, and is thus substantially cuboidal in form. The upper region comprises an aperture 60 therethrough, the aperture 60 being shaped and dimensioned so as to receive a screen. The screen receiving portion 56 thus forms a perimeter which substantially surrounds the entirety of the perimeter of a screen.

The lower region of the screen receiving portion 56 is substantially triangular in form, yet has curved edges. A surface of the lower region of the screen receiving portion 56 which faces outwardly during use of the laryngoscope is substantially flat, or concave, and thus allows a user's thumb to be located on the lower region during use of the laryngoscope 10. The upper and lower regions of the screen receiving portion 56 are integrally formed as part of a single component. The screen receiving portion 56 further comprises an upraised projection 61 on a surface which faces rearwardly during use of the laryngoscope 10. The projection 61 is shaped and dimensioned to be engaged by an upper region of a user's thumb during use of the laryngoscope 10.

The switch button 58 is substantially elliptical in form, and is shaped and dimensioned to be received within the cut-aways 26,48 when the laryngoscope 10 is assembled. The switch button 58 may be connected to a rear surface of the screen receiving portion 56 by a substantially planar retaining member 62, or may be formed as a separate component which is accessible through the cut-aways 26,48.

Each of the first 12, second 14, and third 16 housing components are formed of plastics material and are formed by injection moulding.

Prior to assembly of the laryngoscope 10, a display screen and any associated electronics are assembled, and the display screen is inserted within the screen receiving portion 56. The first 12, second 14, and third 16 housing components are brought together, such that the screen receiving portion 56 of the third housing component 16 is received within the display housing portions 18,40 of the first 12 and second 14 housing components. The housing components 12,14,16 are then joined together by inserting appropriate fasteners through the corresponding apertures 38. Thus the laryngoscope 10, when assembled, is a single unitary housing, which houses any appropriate electronic components, including a camera and a display screen. Furthermore, the lower region of the screen receiving portion 56 and the grip portion 50 allow for convenient location of a user's thumb and forefinger immediately below the display screen, whilst the remainder of the body portion 20 can be securely held by a user's palm and remaining fingers. Such an arrangement may allow for easier manipulation of the laryngoscope 10 without compromising the visibility of the display screen.

In preferred embodiments of the present invention, the camera and the display screen of the laryngoscope are mounted on a flexible circuit board, which may remove the need for expensive connectors between these components. In contrast to conventional laryngoscopes having video capability, where a microprocessor is used to process data between a camera and a display screen, preferred embodiments of the laryngoscope of the present invention comprise a microcontroller which does not take part in data transfer between the camera and the screen, and instead simply carries out initialisation of the camera and the screen.

The invention claimed is:

1. A laryngoscope comprising:
   a display screen component;
   a camera for transmitting images to the display screen component; and
   a microcontroller configured to activate the display screen component and/or the camera, wherein the microcontroller is configured not to process any of the data transferred between the camera and the display screen component, in use,
   wherein the activation of the display screen comprises the microcontroller providing information to the display screen regarding any, or any combination, of power control settings for the display screen, the form of the input signal that will be received from the camera, the format of the image data, and the form of the interface between the microcontroller and the display screen component, or the activation of the camera comprises the microcontroller providing information to the camera regarding any, or any combination, of power control settings for the camera, lens settings for the camera, the form of the output signal that will be provided to the display screen, the format of the image data and any image processing by the camera, and the form of the interface between the microcontroller and the camera.

2. The laryngoscope as claimed in claim 1, wherein the display screen component and the camera cooperate with each other, without the need for any processing of the image data by the microcontroller.

3. The laryngoscope as claimed in claim 1, wherein the information regarding the form of the input signal and/or the image data that will be received from the camera includes information regarding any, or any combination, of orientation, size, color, pixel arrangement, image correction, and overall image data format.

4. The laryngoscope as claimed in claim 1, wherein the information regarding the form of the output signal and/or the image data that will be provided to the camera may include information regarding any, or any combination, of orientation, size, color, pixel arrangement, image correction, and overall image data format.

5. The laryngoscope as claimed in claim 1, wherein the display screen and the camera are adapted, for example during activation, to be supplied by the same input voltage.

6. The laryngoscope as claimed in claim 1 further comprising:
   a body including a handle;
   a laryngoscope blade extending from a distal end of the body; and
   a display screen housing extending from a proximal end of the body, the display screen housing accommodating the display screen component, wherein the laryngoscope comprises at least one unitary housing component that defines at least a portion of each of the body, the laryngoscope blade and the display screen housing.

7. The laryngoscope as claimed in claim 6, wherein the laryngoscope comprises at least two unitary housing components, a first housing component that defines at least a portion of each of the body, the laryngoscope blade and the display screen housing, and a second housing component that defines at least a portion of the body and the display screen housing.

8. The laryngoscope as claimed in claim 6, wherein the display screen housing comprises a display screen component, and a plurality of housing components are brought together to encapsulate the screen component.

9. The laryngoscope as claimed in claim 8, wherein the housing components define an opening, through which the screen component is visible.

10. The laryngoscope as claimed in claim 6, wherein the laryngoscope comprises at least two side housing components, which at least partially define each side of the body and display screen housing of the laryngoscope, relative to a medial plane substantially bisecting the body and the laryngoscope blade.

11. The laryngoscope as claimed in claim 10, wherein the laryngoscope further comprises a rear housing component, which defines an opening through which the display screen of the display screen component is visible.

12. The laryngoscope as claimed in claim 1 further comprising:
    a body including a handle for receiving a palm of a user's hand, in use;
    a laryngoscope blade extending from a distal end of the body;
    a display screen housing extending from a proximal end of the body, the display screen housing accommodating the display screen component; and
    a grip portion being provided for receiving at least a thumb and index finger of the user's hand, in use, the grip portion being located intermediate the display screen component and the handle.

13. The laryngoscope as claimed in claim 12, wherein the grip portion comprises a thumb-receiving surface for receiving at least a portion of a thumb of a user, in use, the thumb-receiving surface being a surface which faces the user, in use, and the thumb-receiving surface of the grip portion comprising a location formation for engagement by at least a portion of a thumb of a user, the location formation being adapted to impede longitudinal movement of the thumb towards the display screen component.

14. The laryngoscope as claimed in claim 12, wherein the location formation comprises an abutment surface for contacting at least a portion of a thumb of the user, in use, the abutment surface having a width that is greater than the width of a tip of a thumb of a user, and outer regions that extend at least partially backwards relative to the tip of the thumb, towards the user's hand, to impede transverse movement of the thumb.

15. The laryngoscope as claimed in claim 12, wherein the grip portion comprises a finger-receiving surface for receiving an index finger of a user in use, the finger-receiving surface including a surface that faces away from a user in use, and the finger-receiving surface being adapted to impede movement of a finger of a user towards the display screen component and towards the handle.

16. The laryngoscope as claimed in claim 15, wherein the finger-receiving surface comprises a recess or depression for receiving at least a portion of an index finger of a user, in use, and the recess or depression is bounded on both sides by a lip or upstanding projection.

17. The laryngoscope as claimed in claim 15, wherein the display screen housing and/or the display screen component are non-removable from the body of the laryngoscope, without disassembling or breaking the body of the laryngoscope.

18. The laryngoscope as claimed in claim 1, wherein the laryngoscope is a single-use, disposable laryngoscope.

* * * * *